United States Patent
Santini, Jr. et al.

(10) Patent No.: US 6,875,208 B2
(45) Date of Patent: Apr. 5, 2005

(54) MICROCHIP DEVICES WITH IMPROVED RESERVOIR OPENING

(75) Inventors: John T. Santini, Jr., Belmont, MA (US); Michael J. Cima, Winchester, MA (US); Norman F. Sheppard, Jr., Bedford, MA (US); Nolan T. Flynn, Brookline, MA (US); Scott A. Uhland, Roslindale, MA (US); Zouhair Sbiaa, Malden, MA (US); John M. Maloney, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 160 days.

(21) Appl. No.: 10/159,550

(22) Filed: May 31, 2002

(65) Prior Publication Data

US 2002/0183721 A1 Dec. 5, 2002

Related U.S. Application Data

(60) Provisional application No. 60/294,818, filed on May 31, 2001.

(51) Int. Cl.[7] .......................... A61K 9/22; A61M 31/00; A61M 37/00
(52) U.S. Cl. ................. 604/890.1; 604/891.1; 604/93.01
(58) Field of Search .................. 604/890.1, 891.1, 604/93.01; 128/898; 216/2, 39, 56

(56) References Cited

U.S. PATENT DOCUMENTS

| | | |
|---|---|---|
| 3,798,141 A | 3/1974 | Yahalom |
| 4,345,981 A | 8/1982 | Bennett et al. |
| 4,360,019 A | 11/1982 | Portner et al. |

(Continued)

FOREIGN PATENT DOCUMENTS

| | | |
|---|---|---|
| DE | 197 16 683 C1 | 6/1998 |
| WO | 01/12157 | 2/2001 |
| WO | 01/35928 | 5/2001 |
| WO | 01/64344 | 9/2001 |

OTHER PUBLICATIONS

BAE, et al., "Pulsatile Drug Release by Electric Stimulus" in *Polymeric Drugs and Drug Administration* Ottenbrite, ed.), ACS Sym. Series (Aug. 23–28, 1992).

Barillaro, et al., "A Porous Silicon LED Based on a Standard BCD Technology," *Optical Materials* 17: 91–94 (2001).

Bhattacharya et al., "Next Generation Integral Passives: Materials, Processes, and Integration of Resistors and Capacitors on PWB Substrates," *J. Mater. Sci–Mater. Electron.* 11(3):253–68 (2000).

(Continued)

*Primary Examiner*—Brian L. Casler
*Assistant Examiner*—Catherine S. Williams
(74) *Attorney, Agent, or Firm*—Sutherland Asbill & Brennan, LLP (57) ABSTRACT

Microchip devices and methods of manufacture thereof are provided to increase the uniformity and reliability of active exposure and release of microchip reservoir contents. In one embodiment, the microchip device for the controlled release or exposure of molecules or secondary devices comprises: (1) a substrate having a plurality of reservoirs; (2) reservoir contents comprising molecules, a secondary device, or both, located in the reservoirs; (3) reservoir caps positioned on the reservoirs over the reservoir contents; (4) electrical activation means for disintegrating the reservoir cap to initiate exposure or release of the reservoir contents in selected reservoirs; and (5) a current distribution means, a stress induction means, or both, operably engaged with or integrated into the reservoir cap, to enhance reservoir cap disintegration.

27 Claims, 5 Drawing Sheets

U.S. PATENT DOCUMENTS

| | | | |
|---|---|---|---|
| 4,507,115 | A | 3/1985 | Kambara et al. |
| 4,585,652 | A | 4/1986 | Miller et al. |
| 4,731,049 | A | 3/1988 | Parsi |
| 4,793,825 | A | 12/1988 | Benjamin et al. |
| 4,994,023 | A | 2/1991 | Wellinghoff et al. |
| 5,042,975 | A | 8/1991 | Chien et al. |
| 5,167,625 | A | 12/1992 | Jacobsen et al. |
| 5,200,051 | A | 4/1993 | Cozzette et al. |
| 5,202,018 | A | 4/1993 | Horanyi et al. |
| 5,252,294 | A | 10/1993 | Kroy et al. |
| 5,304,293 | A | 4/1994 | Tierney et al. |
| 5,318,557 | A | 6/1994 | Gross |
| 5,324,316 | A | 6/1994 | Schulman et al. |
| 5,336,213 | A | 8/1994 | D'Angelo et al. |
| 5,366,454 | A | 11/1994 | Currie et al. |
| 5,368,588 | A | 11/1994 | Bettinger |
| 5,368,704 | A | 11/1994 | Madou et al. |
| 5,427,585 | A | 6/1995 | Bettinger |
| 5,443,508 | A | 8/1995 | Giampapa |
| 5,524,338 | A | 6/1996 | Martyniuk et al. |
| 5,770,076 | A | 6/1998 | Chu et al. |
| 5,797,898 | A * | 8/1998 | Santini, Jr. et al. ...... 604/890.1 |
| 5,824,204 | A | 10/1998 | Jerman |
| 5,824,787 | A | 10/1998 | Singer |
| 5,938,923 | A | 8/1999 | Tu et al. |
| 5,962,081 | A | 10/1999 | Ohman et al. |
| 5,985,328 | A | 11/1999 | Chu et al. |
| 5,989,445 | A | 11/1999 | Wise et al. |
| 6,027,695 | A | 2/2000 | Oldenburg et al. |
| 6,114,658 | A | 9/2000 | Roth et al. |
| 6,123,861 | A | 9/2000 | Santini, Jr. et al. |
| 6,136,212 | A | 10/2000 | Mastrangelo et al. |
| 6,140,740 | A | 10/2000 | Porat et al. |
| 6,171,850 | B1 | 1/2001 | Nagle et al. |
| 2002/0072784 | A1 | 6/2002 | Sheppard, Jr. et al. |
| 2002/0099359 | A1 | 7/2002 | Santini, Jr. et al. |
| 2002/0107470 | A1 | 8/2002 | Richards et al. |
| 2002/0119176 | A1 | 8/2002 | Greenberg et al. |
| 2002/0138067 | A1 | 9/2002 | Sheppard, Jr. et al. |
| 2002/0151776 | A1 | 10/2002 | Shawgo et al. |

OTHER PUBLICATIONS

Frankenthal, et al., "Electroetching of Platinum in the Titanium–Platinum–Gold Metallization on Silicon Integrated Circuits," *Electrochem. Soc*: Solid–State Science Tech. 703–06 (1776).

Izumi, et al., "Activation of a Gold Electrode by Electrochemical Oxidation–Reduction Pretreatment in Hydrochloric Acid," *J. Electroanal Chem.*, 303:151–60 (1991).

Kwon, et al., "Electrically Erodible Polymer Gel for Controlled Release of Drugs," *Nature* 354: 291–293 (1991).

Low, et al., "Microactuators Towards Microvalves for Responsive Controlled Drug Delivery," *Sensors & Actuators B* 67: 149–60 (2000).

Madou et al., "From Batch to Continuous Manufacturing of Microbiomedical Devices," *Chem. Rev.*, 100: 2679–2692 (2000).

Madou et al., "Exploitation of a Novel Artificial Muscle for Controlled Drug Delivery," pp. 495–497 (1999).

Surbled, et al., "Characterization of Sputtered TiNi Shape Memory Alloy Thin Films, " *Jpn. J. Appl. Phys.*, 38:L1547–L1549 (1999).

Surbled, et al., "Array of Shape Memory Alloy One–shot Micro–Valves for Drug Delivery," MME '99, Gif Sur Yvette, France (Sep. 27–28, 1999).

Surbled, et al., "Shape Memory Alloys for Micromembranes Actuation," SPIE, 3825:63–70 (1999).

Tierney, et al., "Electroreleasing Composite Membranes for Delivery of Insulin and Other Biomacromolecules," *J. Electrochem. Soc.*, 137:2005–2006 (1990).

Tierney, et al., et al., "New Electrorelease Systems Based on Microporous Membranes," *J. Electrochem. Soc.*, 137:3789–3793 (1990).

* cited by examiner

Spring Design:

FIG. 5

Cross Section of the Spring Configuration:

MICROCHIP DEVICES WITH IMPROVED RESERVOIR OPENING

CROSS-REFERENCE TO RELATED APPLICATIONS

Priority is claimed under 35 U.S.C. §119 to U.S. provisional application Ser. No. 60/294,818, filed May 31, 2001.

BACKGROUND OF THE INVENTION

This invention relates to miniaturized devices for the controlled exposure or release of molecules such as drugs and/or secondary devices such as sensors.

U.S. Pat. No. 5,797,898 to Santini Jr., et al. discloses microchip delivery devices which have a plurality, typically hundreds to thousands, of tiny reservoirs in which each reservoir has a reservoir cap positioned on the reservoir over the molecules, so that the chemical molecules (e.g., drugs) are released from the device by diffusion through or upon disintegration of the reservoir caps. The reservoirs may have caps made of a material that degrades at a known rate or that has a known permeability (passive release), or the caps may include a conductive material capable of dissolving or becoming permeable upon application of an electrical potential (active release).

In the active release devices, the reservoir cap can be a thin metal film. Application of an electric potential causes the metal film to oxidize and disintegrate, exposing the contents of the reservoir to the environment at the site of the microchip device. It would be advantageous to enhance this oxidation and disintegration across the surface of the metal film, in order to achieve consistent and reliable exposure of the molecules and secondary devices contained in the reservoirs. It would be particularly desirable, for example, to provide microchip devices that provide highly reliable and precise exposure of drug molecules located in reservoirs in the microchip delivery devices to the environment in which the microchip device is implanted. More generally, it would be desirable to provide devices and methods to enhance the opening of reservoir caps in microchip devices for the controlled exposure or release of reservoir contents.

SUMMARY OF THE INVENTION

Microchip devices and methods of manufacture thereof are provided to increase the uniformity and reliability of active exposure and release of microchip reservoir contents. In one embodiment, the microchip device for the controlled release or exposure of molecules or secondary devices comprises: (1) a substrate having a plurality of reservoirs; (2) reservoir contents comprising molecules, a secondary device, or both, located in the reservoirs; (3) reservoir caps positioned on the reservoirs over the reservoir contents; (4) electrical activation means for disintegrating the reservoir cap to initiate exposure or release of the reservoir contents in selected reservoirs; and (5) a current distribution means, a stress induction means, or both, operably engaged with or integrated into the reservoir cap, to enhance reservoir cap disintegration.

The device can further include a cathode, wherein the reservoir caps each comprise a thin metal film which is an anode, the electrical activation means comprises a means for applying an electric potential between the cathode and the anode effective to cause the reservoir cap disintegration to occur electrochemically. The device can, alternatively or in addition, further include at least one resistor operably adjacent the reservoir caps, wherein the electrical activation means comprises a means for applying an electric current through the resistor effective to cause the reservoir cap disintegration to occur thermally.

In one embodiment, the current distribution means can comprise a current distribution network mounted on or integrated into the reservoir cap. In another embodiment, the current distribution means can include an electrochemically plated metal layer on the outer surface of the reservoir cap, wherein the metal layer has increased surface roughness relative to the outer surface of the reservoir cap. The stress induction means can comprise a pre-stressed structure attached to or integrated into the reservoir cap, the pre-stressed structure providing a force substantially perpendicular to the surface of the reservoir cap. In one embodiment, the pre-stressed structure comprises a bilayer cantilever beam. In other embodiments, the pre-stressed structure has a spring, coil, or cross structure.

Methods of fabricating and using these devices are also provided.

DETAILED DESCRIPTION OF THE INVENTION

It has been discovered that reservoir cap opening in microchip devices can be enhanced by a number of means. Generally speaking, these means include a current distribution means, a stress induction means, or both, operably engaged with or integrated into the reservoir cap, to enhance reservoir cap disintegration.

I. Non-Uniformity of Thin Film Dissolution/Corrosion

Experiments have shown that the electrochemical dissolution rate of some metal membranes may not be uniform or complete across the surface of the membrane. Scanning electron micrographs taken of a partially dissolved gold membrane show the corners and edges of the membrane can corrode more than the interior surface, leaving for example a "flap" of gold still attached to one edge of the electrode. Such a flap may fold over and expose the reservoir opening or may remain in place and partially occlude the reservoir. Other membranes may corrode or dissolve to a certain thickness and then stop before the membrane is structurally weak enough to fall apart or disintegrate. This "residual" membrane may have enough strength to remain intact, thereby hindering or preventing the opening of the reservoir and the release of molecules or exposure of devices contained therein.

Figure 1A:
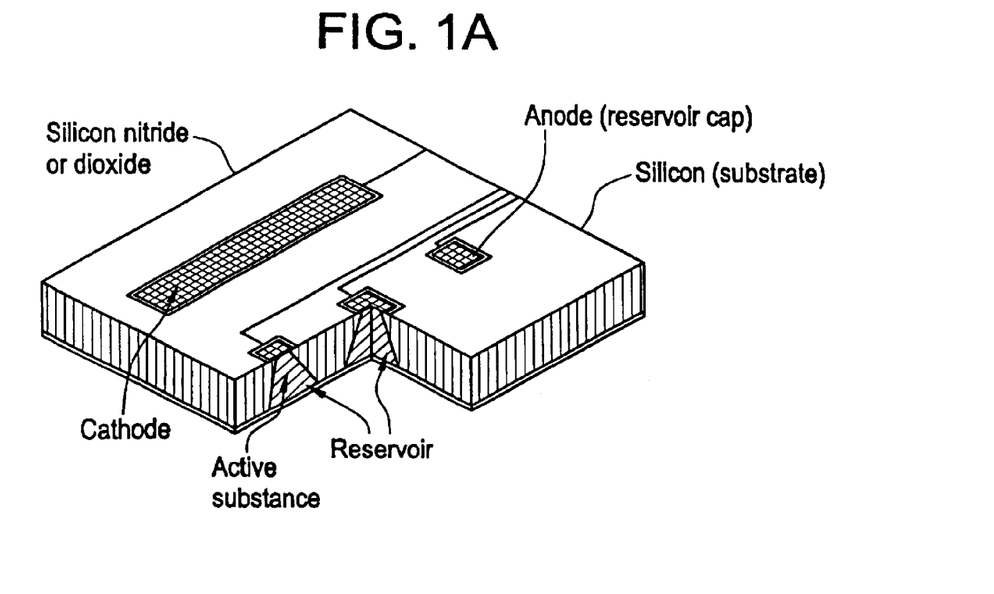
FIG. 1a is perspective diagram of one embodiment of a microchip chemical delivery device, in partial cross-section showing chemical filled reservoirs and membrane reservoir caps.
Figure 1B:
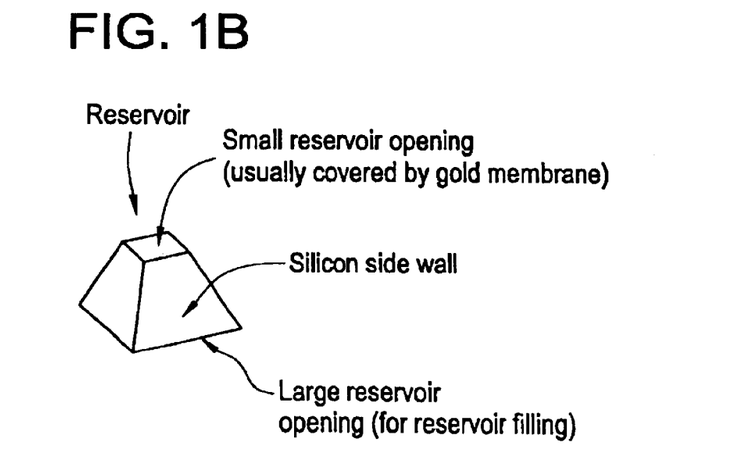
FIG. 1b shows the shape of the reservoir.
Figure 2:
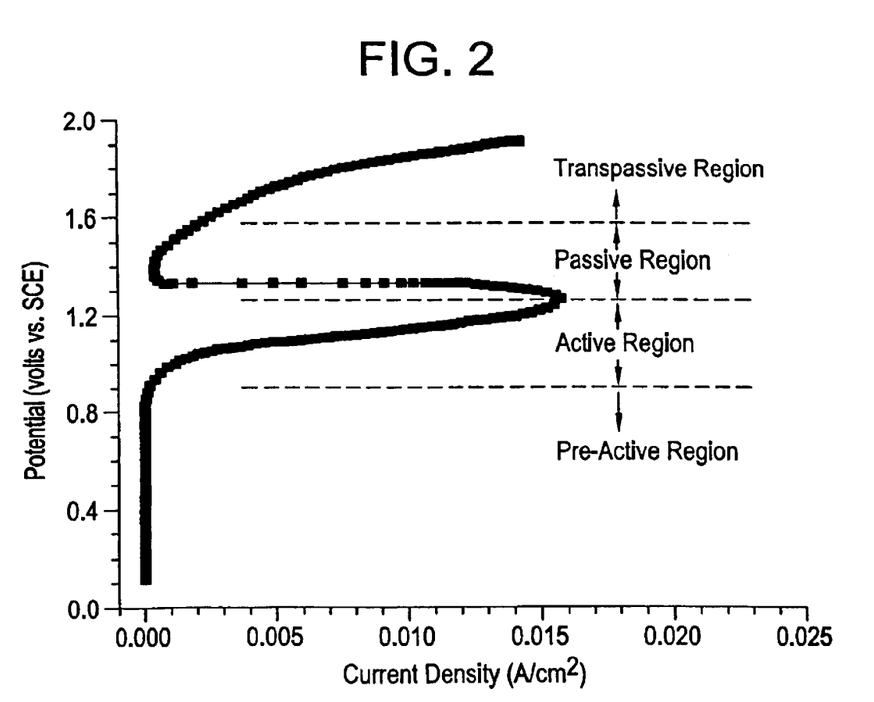
FIG. 2 is a graph showing cyclic voltammetry data for gold in 0.145 M NaCl solution (pH=5.5–6.0), wherein the current peak at 1.0–1.2 volts is associated with the active dissolution of gold.

It is hypothesized that non-uniform or incomplete corrosion of thin metal membranes, such as those serving as reservoir caps, is due to one or a combination of five causes. The first cause is the presence of a non-uniform potential distribution across the surface of the membrane. The potential near the edge is fixed by the material (e.g., glass, silicon) covering the trace (e.g., gold) that supplies electric current to the membrane. However, the electrical resistivity of the membrane rises as it thins during the corrosion process, thus causing the electrical potential to vary across the exposed portion of the membrane, with the lowest potential occurring near the center of the membrane. The potential may become sufficiently low so that the gold corrosion reaction is no longer possible. For example, the potential vs. current diagram shown in FIG. 2 for a gold membrane in a dilute saline solution shows the current peak around 1.0–1.2 volts, which indicates gold corrosion is occurring. The diagram shows that a small decrease in electric potential will cause the corrosion reaction to dramatically decrease or even stop, as indicated by a sharp drop in current. This phenomenon is similar to non-uniform deposition during metal plating processes where the potential drop along metal traces influences the local deposition rate of metal.

The second suspected cause of variation in the rate and degree of metal membrane corrosion is the possible presence of local variations in the composition of the electrolyte at the surface of the metal film. The corrosion process can cause local variations in the composition, pH, and/or temperature of the electrolyte when transport of reactants to the metal surface and/or transport of products away from the metal surface are limited. Such variations in the electrolyte may then result in local surface corrosion rates that differ significantly from corrosion rates of the metal exposed to the bulk electrolyte. Such variations in the electrolyte often occur in or near physical defects such as pits, cracks, crevices, or hillocks, or fabricated structures such as trenches, holes, the interface between two layers of material, or any other location where mass transport may be hindered.

The third possible cause of variation in the rate and degree of uniformity of corrosion of thin metal membranes in microchips is related to their structural morphology, in particular grain size within the metal. For example, gold thin films have been shown to corrode preferentially in grain boundaries with an applied potential in dilute saline solutions (Santini, "A Controlled Release Microchip", Ph.D. Thesis, Massachusetts Institute of Technology, 1999). Increased rates of corrosion in metal grain boundaries can cause portions of the metal film to be isolated from the source of electric potential, resulting in the local stoppage of corrosion. This is a particularly common problem for metal films whose thickness is only one grain thick, because corrosion through the thickness of the membrane or thin film can occur faster than the bulk of the membrane corrodes, which can hinder the passage of current through the membrane and stop the corrosion of the membrane prematurely, thereby potentially leaving portions of the metal membrane un-corroded and intact to hinder chemical release from the reservoirs of the microchip.

The fourth cause is changing internal stress in the metal membrane. Internal mechanical stress in the metal film can influence the corrosion rate. As the film is disintegrated, the force of this stress increases inversely with the decreasing thickness of the film, thereby creating micro-fractures, which expose more surface area to be disintegrated. In addition, stresses at the corners or along the edges of the membrane may be much higher than other regions of the membrane, leading to non-uniform, stress dependent variations in corrosion of the membrane.

The fifth cause of variation is related to the fabrication of thin metal film electrodes. The electron beam and sputtering processes used to deposit thin metal films result in surfaces that are relatively smooth on the atomic scale. This yields inefficient charge transfer and low currents for the geometric areas occupied by the film. In addition, the microfabrication processes used to make the microchip devices may introduce contaminants that adhere strongly to the metal electrode surfaces. Contaminants and the smooth surface of the electrodes can create non-uniform corrosion of the membrane electrodes. Specifically, when an anodic potential sufficient to corrode the metal is applied to the membrane, only a small amount of corrosion occurs until the surface roughens. Instabilities are created when localized regions (for example, the corners of the membrane) roughen before the remainder of the film. These regions have a much higher charge transfer rate and corrode faster. The entire process leads to non-uniform corrosion of the membrane. Removal of these contaminants and roughening of the metal surface will generally result in better electrochemical activity and corrosion.

II. Methods and Devices for Enhanced Reservoir Cap Disintegration

In a preferred embodiment, the microchip device for the controlled release or exposure of molecules or secondary devices comprise: (1) a substrate having a plurality of reservoirs; (2) reservoir contents comprising molecules, a secondary device, or both, located in the reservoirs; (3) reservoir caps positioned on the reservoirs over the reservoir contents; (4) electrical activation means for disintegrating the reservoir cap to initiate exposure or release of the reservoir contents in selected reservoirs; and a current distribution means, a stress induction means, or both, operably engaged with or integrated into the reservoir cap, to enhance reservoir cap disintegration.

As used herein, the terms "electrical activation" in reference to means for disintegrating refers to reservoir cap disintegration that is initiated by application of an electrical current or potential. This disintegration can be primarily as due to electrochemical action or thermal action (i.e. can occur electrochemically or thermally). Electrochemical disintegration occurs when the microchip device is in the presence of an electrolytic solution and comprises a cathode and an anodic reservoir cap (e.g., a thin metal film) and the electrical activation means applies an electric potential between the cathode and the anode effective to cause the reservoir cap to corrode and fall apart, as described for example in U.S. Pat. No. 5,797,898. Thermal activation occurs when the microchip device comprises at least one resistor (i.e. resistive heater) operably adjacent the reservoir cap and the electrical activation means applies an electric current through the resistor effective to heat the reservoir cap or contents enough to cause the reservoir cap to rupture, melt, or otherwise lose structural integrity, as described in PCT WO 01/12157. The device also can be configured so that the heating induces stress forces in the reservoir cap to facilitate mechanical failure. By "operably adjacent" is meant that the resistor is inside the reservoir, or attached to or otherwise sufficiently near the reservoir cap, to transfer an effective amount of heat to the reservoir cap or to the reservoir contents. These types of disintegration can occur together. For example, heating at the reservoir cap can increase the rate of the electrochemical reaction.

A. Current Distribution Means

The current distribution means includes, but is not limited to, structures designed to disperse electrical current and/or thermal energy uniformly across the reservoir cap, as well as structures that increase the exchange current density of reservoir caps that operate as electrodes. Representative current distribution means include current distribution networks and electrochemically plated metal layers (on the outer surface of the reservoir cap) that have increased surface roughness relative to the outer surface of the reservoir cap.

Current Distribution Networks

Effective disintegration is enhanced by providing the thin film with a current distribution network, such as one comprised of a plurality of traces attached to the outer surface of the thin film. The traces (which are strips of metal or another conductor fabricated onto the reservoir caps) and the thin film can be formed of the same material, such as gold, or the traces can be formed of a first material that corrodes at a different rate than a second material of which the thin film is formed. The traces could also be made of a conducting material that does not corrode, such as platinum, titanium, or silicon doped with ionic species. Alternatively, the traces can be coated with a passivating layer, such as one formed of silicon nitride, silicon oxide, or titanium oxide, to aid in the uniform distribution of the corrosion current across the surface of the thin film.

When electrochemical disintegration is to be employed, the current distribution network is a low electrical resistance path on top of, under, or near the membrane (reservoir cap). The current distribution network continues to conduct electricity throughout the duration of the corrosion process, even if the majority of the thin film or membrane anode is losing or has lost its ability to conduct electricity. When thermal disintegration is to be used, the current distribution network is a high electrical resistance path on top of, under, or near the membrane (reservoir cap). That is, it is essentially a resistor that heats the reservoir cap material or the reservoir contents.

Figure 3:
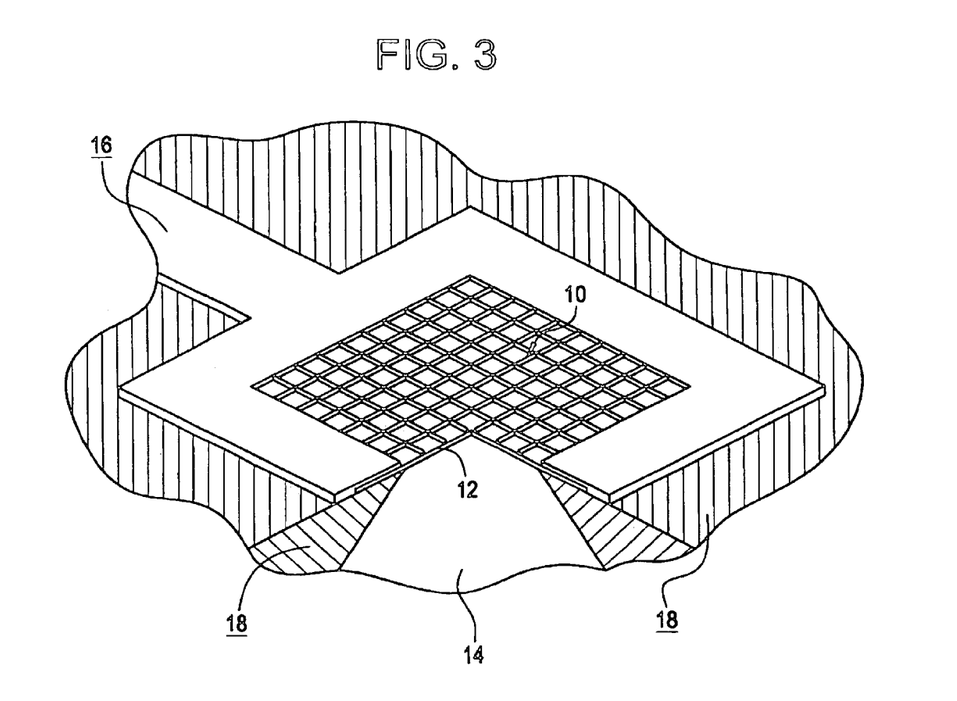
FIG. 3 is a perspective diagram of one embodiment of a reservoir covered by a membrane having a current distribution network.

In a preferred embodiment, a current distribution network is provided on or below the metal membrane (reservoir cap) in order to corrode the metal membrane more uniformly, minimizing the effects of some or all of the non-uniformity factors described above. One embodiment of this network is shown in FIG. 3, which shows current distribution network 10 (which is composed of numerous network traces) fabricated on top of the metal membrane 12 covering reservoir 14. Main trace 16, on substrate 18, provides current to the current distribution network 10 and metal membrane 12. A wide variety of network topologies are suitable. The main traces and network traces can be fabricated from the same or different materials.

The network traces can be current conductor paths that either do not corrode at the potential applied to the membrane or are so thick that their change in resistivity does not change significantly over the period during which they are corroded. Thus, the voltage drop along these traces is insignificant over the period in which the membrane is corroding. The traces simply act as current distribution "busses." These traces can be located either on top of or below the membrane.

The trace spacing should be chosen to insure that the potential affected zone of the membrane is always close to one of the traces. This spacing can be established by measurement of the membrane resistivity as a function of thickness and by knowledge of the membrane thickness at which the membrane no longer retains structural integrity. The membrane resistivity will rise rapidly as the film becomes thinner. The resistivity at the failure thickness and the applied current density will establish the potential drop over film between the traces. This current distribution network will also form numerous crevices along the surface of the membrane. If crevice corrosion is indeed a significant contributor to corrosion for the particular metal/electrolyte system, then this process will allow the membrane to corrode more reproducibly by increasing the surface areas at which the membrane will corrode, perforate, and thereby expose and release molecules or devices from the reservoir.

In another preferred embodiment, a current distribution network is provided on top of the metal membrane (reservoir cap) by suitably patterning an insulating layer, in order to allow the portions of the membrane below the insulating layer to corrode slower, enabling those portions of the membrane to remain at the corrosion potential and distribute the corrosion current to neighboring exposed membrane surfaces as they become thinner. Preferred materials for such non-conducting layers include oxides and nitrides of silicon, titanium, and chromium, carbides, diamond-like materials, and certain organic compounds such as photopolymers (photoresists, polyimide), fluoropolymers (e.g. TEFLON™) and some epoxies.

Distribution Network Traces

The traces may be composed of several different types of materials. In one embodiment, the network traces are composed of the same material as the membrane or film, such as gold or other metals described above. In this embodiment, however, the traces are substantially thicker in cross-sectional area, such that the traces will corrode when the potential is applied, but the change in resistivity will be small compared to that which occurs in the membrane.

In another embodiment, the network traces are fabricated from a metal that does not corrode at the same potential as the membrane material. For example, platinum or titanium trace materials can be used with gold membranes.

In still another embodiment, the network traces are metal coated with a passivating layer to prevent degradation or corrosion. In a preferred form of this embodiment, gold network traces are coated with silicon oxide or silicon nitride dielectrics. In another variation, a current distribution network is provided on top of the metal membrane (reservoir cap) by patterning an insulating layer, in order to allow the portions of the membrane below the current distribution network to corrode slower, enabling those portions of the membrane to remain at the corrosion potential and distribute the corrosion current to neighboring exposed membrane surfaces as they become thinner. Preferred materials for such non-conducting layers include oxides and nitrides of silicon, titanium, and chromium, carbides, diamond-like materials, and certain organic compounds such as fluoropolymers (e.g. polytetrafluoroethylene) and some epoxies.

Increased Surface Roughness

In another embodiment, the current distribution means includes a reservoir cap or a layer thereon having a roughened metal surface for distributing current uniformly across the surface of the anode. The roughened surface transfers charge efficiently and should result in more uniform corrosion. Typically, the roughening method involves either repeated potential cycling through the metal oxide formation and stripping regions or repeated cycling in a metal complexing solution such as that containing a halide salt. The first method drives oxygen many atomic lengths into the surface and then removes it, potentially in combination with some metal. The latter method specifically dissolves and redeposits metal.

In one embodiment, roughening of the metal anode surface is obtained by plating a small amount of metal under conditions that should yield a nonepitaxial film. In the case of gold anodes, for example, a solution containing a mildly oxidizing, non-halide containing electrolyte such as $HNO_3$, $KNO_3$, $H_2SO_4$, $Na_2SO_4$ is prepared at a concentration between 0.01 and 5 M. To this solution, a small amount of $HAuCl_4$ or other gold salt is added. The concentration of the gold salt should be in the range of 1 to 500 nM per $cm^2$ of gold surface area on the device of interest. This concentration range ensures that no more than a few hundred atomic layers of gold will be deposited. The gold-containing device is then externally connected to a potential source such as a potentiostat. The device is then immersed in the above solution along with a counter and working electrode. The counter electrode is a clean, large surface area gold wire, sheet or mesh, which can act as an additional gold ion source. The most useful reference electrodes for this procedure are non-halide containing electrodes such as $Hg|Hg_2SO_4|K_2SO_4$ or $Hg|HgO|NaOH$. Physically isolating the reference electrode by placing it in a beaker connected by a salt bridge or Luggin capillary will minimize contamination. After immersion and electrical connection, a potential waveform (i.e., a square, triangular, or saw-tooth) is applied to the system using the standard three-electrode electrochemical cell geometry. This waveform scan or step is bounded by an upper potential limit of 1.0 to 2.0 V and a lower limit of –0.5 to 0.5 V. The upper limit is in the range where some oxide formation will occur. The lower limit is below the oxide-stripping region and also below the gold reduction region. The presence of the small quantity of gold salt in the solution prevents substantial dissolution of gold and provides material to be plated on the existing gold surface. After continued potential cycling for a period of 10 seconds to 1 hour, the cycling is stopped at the lower potential limit. The device is then withdrawn from the gold solution under potential control at this lower limit. This will ensure that the open circuit potential does not allow removal or oxidation of the gold immediately before withdrawal.

Electrochemical dissolution of a reservoir cap can be enhanced by cleaning and roughening the electrode surface. Examples of techniques for surfacing roughening include (1) increasing the electrode surface area by electrochemically plating metal onto the surface of the electrode prior to use and (2) repeatedly cycling the metal electrode through the oxide formation and stripping potentials.

B. Stress Induction Means

Internal stress in the reservoir cap can be controlled, induced, and distributed by several techniques. When the metal film is fabricated, its initial tension can be adjusted by varying the shape of the support layer used in the deposition of the metal. For example, a flat support will result in a higher residual stress than a concave or convex support layer because the flat support will produce a tighter film when the film cools. Also, additional thickness of metal could be added to known high stress areas, such as corners, to extend the time required for sufficient disintegration in these areas where disintegration would occur at a faster rate due to the combination of the primary [electro] corrosion and the stress which is creating micro fractures. The stress can be controlled by patterning another material (conducting or non-conducting) on either or both sides of the metal film. This process would retard disintegration selectively and would reinforce the metal film in specific locations. For example, a pattern of the top surface dielectric that is used to insulate the electrical conductors that has rounded corners where it terminates at the periphery of the metal caps would produce less localized stress than sharp (e.g. 90°) corners. A pattern that extended over the central area of the metal cap could also distribute loading, thereby reducing local stress concentration.

Another factor that will control the magnitude and sign (tension vs. compression) of these stresses is the thermal processing history of the film. Thermal stresses can develop from a difference in thermal expansion between the film and the substrate on cooling the film from process temperature(s) to room temperature. By controlling the thermal cycle and engineering specific thermal mismatch differences, one can target specific stressed states. In one embodiment, the stress inducing means comprises a pre-stressed structure that enhances reservoir cap opening, for example, as the reservoir cap thermally or electrochemically disintegrates. The pre-stressed structure preferably provides a force substantially perpendicular to the surface of the reservoir cap.

The pre-stressed structure can be a member attached to (e.g., built upon) or integrated into the reservoir cap. Residual stress in the structure, in its simplest form, a cantilever beam, loads the membrane. The intact membrane counteracts the stress. As the membrane corrodes and weakens, the stress introduced by the structure exceeds the yield strength of the corroded membrane and the structure penetrates the membrane.

Figure 4:
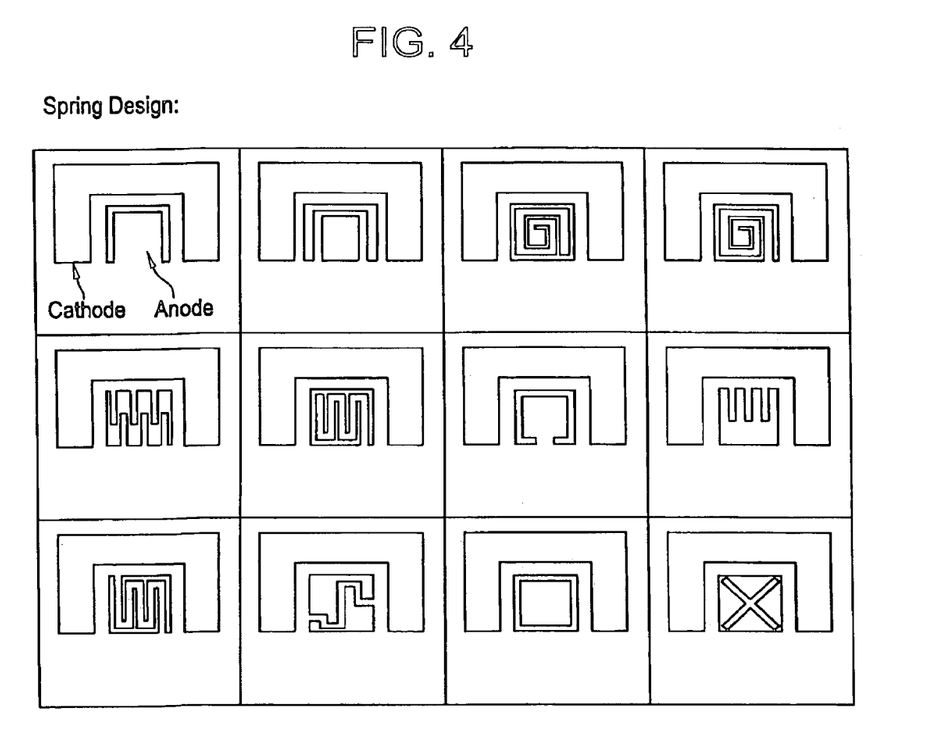
FIG. 4 is a plan view of twelve possible designs of springs to fabricate onto the reservoir caps of microchip devices, wherein the springs serve as stress-inducing structures to facilitate disintegration/rupture of the reservoir caps.
Figure 5:
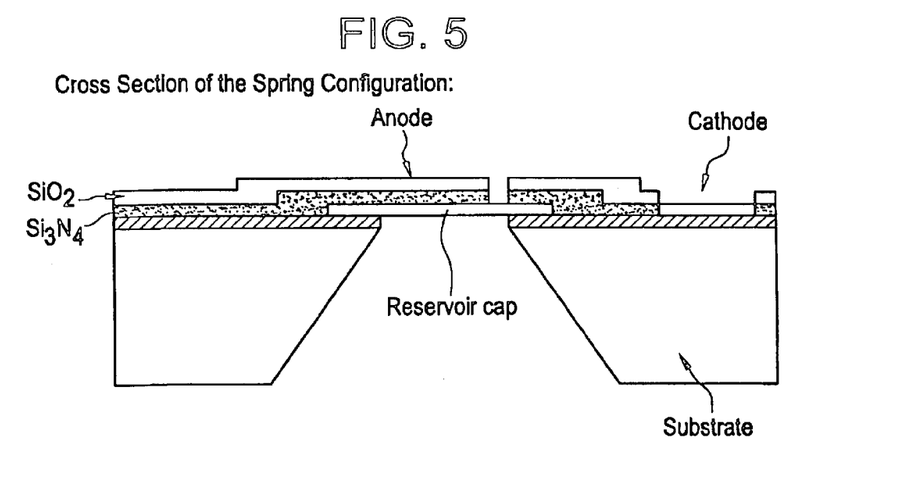
FIG. 5 is a cross-sectional view of one embodiment of a microchip device having a spring stress inducing structure.

In one embodiment, the pre-stressed structure is a cantilever beam, e.g., located on a thin film anode. This beam will cause the reservoir to open if the anode corrodes or dissolves to a certain thickness and then stops before the membrane is structurally weak enough to fall apart. In other embodiments, the pre-stressed structure can comprise a single layer of material having a stress gradient, or the pre-stressed structure can comprise a spring, coil, or cross design (see FIGS. 4 and 5), as well as a variety of other configurations.

In another approach, a structure is fabricated as a composite of two layers having residual stress of opposite sign. That is, one layer having a built-in tensile stress, while the other having a compressive stress. The means to control stress in thin films deposited during microfabrication is well known. For example, the stress of films deposited using plasma-enhanced chemical vapor deposition (PECVD) is controlled by controlling the temperature of the deposition, and the composition of the gases used to form the film. A suitable structure can be formed of a composite layer of silicon dioxide having a compressive stress, and a layer of silicon nitride having a tensile stress.

By controlling internal stress levels and the distribution of internal stresses in the metal film, a more consistent corrosion result can be achieved. Stress levels can be controlled by, for example, varying the dimensions of the metal film (including thickness), its grain size and crystal orientation, the film's intrinsic stress (affected by parameters such as temperature, pressure, and method of deposition), and its initial tension loading, as well as by selective patterning of other materials on the top and/or bottom surfaces of the metal film to direct the stress loading of the film (while still exposing a sufficient amount of metal film to achieve effective disintegration).

C. Controlled Morphology of the Metal Membrane

Where grain boundary corrosion is a dominant cause of non-uniform corrosion and molecule release, reliability and uniformity can be improved by changing the structural morphology (i.e. average grain size distribution and grain orientation distribution) of the metal membrane itself. Specifically, decreasing the size of the metal grains with respect to the thickness of the membrane should improve corrosion of the membrane, and thus opening of the reservoir and release of molecules. This grain size change will increase the proportion of the membrane mass and metal surface area consisting of grain boundaries with respect to the mass and metal surface area consisting of grains. Therefore, preferential corrosion of the grain boundaries will cause a larger portion of the membrane to corrode, leaving a membrane that is weaker and more likely to open after corrosion by an applied potential.

There are numerous methods (e.g., plasma-deposition or evaporation-deposition) with several parameters (e.g., impurity level, temperature, and deposition potential) to keep grain sizes small in thin films. See for example, Thompson, "Grain Growth in Thin Metal Films," *Annu. Rev. Mater. Sci.,* vol. 20, pp. 245–68 (1990); King & Harris, "Grain Growth Suppression and Enhancement by Interdiffuision in Thin Metal Films", *Mat. Res. Soc. Symp. Proc.,* vol. 343, pp. 33–42 (1994). In one embodiment, the metal is deposited at a higher base pressure (e.g. lower base vacuum), which typically is greater than $10^{-5}$ Torr. This allows oxygen and other impurities in the deposition chamber to be incorporated into the metal film. These impurities can slow grain boundary mobility and grain growth. Impurities can also be introduced into grain structure by solution doping. "Impurities" present in solution are capable of strongly influencing the grain growth rate, since they will tend to segregate to the grain boundaries and exert a drag force on boundary motion. These impurities can also be in the form of precipitates. The grain boundaries must move past the precipitates during growth, which results in a local increase in interfacial energy that acts as an impeding force on the grain boundary.

The thermal processing of the metal film is a critical factor that dictates the average grain size and the size distribution because grain boundary mobility is strongly temperature dependent, $M^{grain} \propto \exp^{(-E/kT)}$. Therefore, grain size can be kept small by limiting thermal processing of the thin film after deposition, as high temperatures can induce high grain growth rates, i.e. large grains. Maintaining low temperatures during processing, $T<0.2*T^{Melt}$, will promote a smaller average grain size (10 to 100 nm), while higher temperatures, $T>0.2*T^{Melt}$, will yield larger grains ($\geq 1000$ nm).

Since corrosion may occur primarily at the "amorphous" grain boundaries, the gold film may preferably be amorphous rather than polycrystalline. This may be achieved by impurity doping and/or rapid cooling in excess of $10^8$ K/sec during processing (Schaffer, et al., *The Science and Design of Engineering Materials,* p. 225, Irwin Inc. (Chicago 1995)). Another potential method for producing amorphous metal films involves bombarding the metal film during deposition with an ion beam.

Effective disintegration is enhanced by controlling the size of the grains in the metal film. For example, the longest dimension of metal grains possibly may be made smaller than the thickness of the film. Small grain size can be achieved, for example, by forming the metal film via deposition at a high base pressure (i.e. lower base vacuum). Large grain size, if desired, can be achieved by deposition of the metal film at high vacuum. Grain size may also be modified by impacting the thin film with an ion beam during deposition. Small grain size can be maintained by avoiding exposure to high temperatures following deposition of the metal film, while grains can be made larger by post-deposition heat treatment.

III. The Basic Microchip Devices

As used herein, a "microchip" is a miniaturized device fabricated using methods commonly applied to the manufacture of integrated circuits such as ultraviolet (UV) photolithography, reactive ion etching, and electron beam evaporation, as described, for example, by Wolf & Tauber, *Silicon Processing for the VLSI Era, Volume 1—Process Technology* (Lattice Press, Sunset Beach, Calif., 1986); and Jaeger, *Introduction to Microelectronic Fabrication,* Volume V in *The Modular Series on Solid State Devices* (Addison-Wesley, Reading, Mass., 1988) ), as well as MEMS methods that are not standard in making computer microchips, including those described, for example, in PCT WO 01/41736; Madou, *Fundamentals of Microfabrication* (CRC Press, 1997); and other micromolding and micromachining techniques known in the art. The microchips provide control over the rate the molecules are released as well as the time at which release begins. The time of release can be controlled actively or passively.

The microchip fabrication procedure allows the manufacture of devices with primary dimensions (length of a side if square or rectangular, or diameter if circular) ranging from less than a millimeter to several centimeters. Typical device thicknesses range from 300 to 550 $\mu$m. However, the thickness of the device can vary from approximately 10 $\mu$m to several centimeters, depending on the device's application. Total device thickness and reservoir volume can also be increased by bonding (for example, by anodic bonding) or attaching (for example, by adhesives) additional silicon wafers or other substrate materials (such as glasses or plastics) having openings or apertures that align with the reservoirs to the fabricated microchip device. In general, changing the device thickness affects the volume of each reservoir and may affect the maximum number of reservoirs that may be incorporated onto a microchip. In vivo applications of the device typically require devices having a primary dimension of 5 cm or smaller. Devices for in vivo applications may be made small enough to be swallowed or implanted using minimally invasive procedures. Smaller in vivo devices (on the order of a millimeter) can be implanted using a catheter or other injectable means. Devices for in vitro applications have fewer size restrictions and, if necessary, can be made much larger than the dimension ranges for in vivo devices.

IV. Device Components and Materials

Each device consists of a substrate, reservoirs, and a release system containing, enclosing, or layered with the molecules to be delivered. The device further includes a reservoir cap to control the release or exposure time of the molecules or devices contained in the reservoirs, and typically includes control circuitry and a power source for active microchips. The substrate, reservoirs, release system, reservoir contents, control circuitry and power source are substantially as described in U.S. Pat. Nos. 5,797,898 and 6,123,861, as well as PCT WO 02/30401, WO 02/30264, WO 01/91902, WO 01/64344, WO 01/41736, WO 01/35928, and WO 01/12157.

A. The Substrate

The substrate contains the etched, machined, or molded reservoirs and serves as the support for the microchip. Any material which can serve as a support, is suitable for etching, machining, or molding, and is impermeable (during the time scale of the microchip's use) to the molecules to be delivered and to the surrounding fluids (e.g., water, blood, electrolytes or other solutions) may be used as a substrate. Examples of substrate materials include metals, ceramics, semiconductors, and degradable and non-degradable polymers. Biocompatibility of the substrate material is preferred, but not required. For in vivo applications, non-biocompatible materials may be encapsulated or contained in a biocompatible material, such as poly(ethylene glycol), polytetrafluoroethylene-like materials, or titanium, before use. One example of a strong, non-degradable, easily etched substrate that is impermeable to the molecules to be delivered and the surrounding fluids is silicon. In another embodiment, the substrate is made of a strong material that degrades or dissolves over a defined period of time into biocompatible components. This embodiment is preferred for in vivo applications where the device is implanted and physical removal of the device at a later time is not feasible or recommended, for example, brain implants. An example of a class of strong, biocompatible materials are the poly (anhydride-co-imides) described in Ulhrich et al., "Synthesis and characterization of degradable poly(anhydride-co-imides)", *Macromolecules*, 28:2184–93 (1995). Another group of biocompatible polymers suitable for use as a substrate material includes PLA [poly(lactic acid)], PGA [poly(glycolic acid)], and PLGA [poly(lactic-co-glycolic acid)].

B. Molecules and Secondary Devices (Reservoir Contents)

The reservoirs contain molecules, secondary devices, or combinations thereof, that need to be protected from surrounding environmental components until their release or exposure is desired. Proper functioning of certain reservoir contents, such as a catalyst or sensor, generally does not require their release from the reservoir; rather their intended function, e.g., catalysis or sensing, occurs upon exposure of the reservoir contents to the environment outside of the reservoir after opening of the reservoir cap. Thus, the catalyst molecules or sensing component can be released or can remain immobilized within the open reservoir.

Molecules

The reservoir contents can include essentially any natural or synthetic, organic or inorganic molecule or mixture thereof, for release (i.e. delivery) or retained and exposed. The molecules (i.e. chemicals) may be in pure solid, liquid, or gel form, or mixed with other materials that affect the release rate and/or time. Chemicals may be in the form of solid mixtures including, but not limited to, amorphous and crystalline mixed powders, monolithic solid mixtures, lyophilized powders, and solid interpenetrating networks; in the form of liquid mixtures including, but not limited to, solutions, emulsions, colloidal suspensions, and slurries; and in the form of gel mixtures including, but not limited to, hydrogels.

For in vivo applications, the chemical preferably is a therapeutic, prophylactic, or diagnostic agent. In one embodiment, the microchip device is used to deliver drugs systemically to a patient in need thereof. In another embodiment, the construction and placement of the microchip in a patient enables the local or regional release of drugs that may be too potent for systemic delivery of an effective dose. As used herein, "drugs" include any therapeutic, prophylactic or diagnostic agent, including organic or inorganic molecules, proteins, nucleic acids, polysaccharides and synthetic organic molecules, having a bioactive effect. Representative examples include analgesics, steroids, cytokines, psychotropic agents, chemotherapeutic agents, and hormones anesthetics, vaccines, metabolites, sugars, immunomodulators, antioxidants, ion channel regulators, and antibiotics. An example of a diagnostic agent is an imaging agent such as a contrast agent. The drugs can be in the form of a single drug or drug mixtures and can include pharmaceutically acceptable carriers.

In another embodiment, molecules are released in vitro in any system where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures.

In another embodiment, the molecules to be released are perfumes, fragrances, dyes, coloring agents, sweeteners, or a variety of other compounds, which for example, may be useful to release as a function of temperature change.

In other embodiments, the reservoirs contain immobilized molecules. Examples include any chemical species which can be involved in a reaction, including, but not limited to, reagents; catalysts, including enzymes, metals, and zeolites; proteins; nucleic acids; polysaccharides; polymers; cells, as well as organic or inorganic molecules, including diagnostic agents.

Formulations of molecules to be released also may contain stabilizers and anti-oxidants to preserver the integrity of the drug or other molecules.

Molecules to be delivered may be inserted into the reservoirs in their pure form, as a liquid solution or gel, or as a material that quickly vaporizes. Alternatively, the molecules may be encapsulated within or by a release system. As used herein, "release system" includes both the situation where the molecules are in pure form, as either a solid, liquid, or vapor, or are formulated in a matrix formed of a degradable material or a material that releases incorporated molecules by diffusion out of or disintegration of the matrix. The degradation, dissolution, or diffusion properties of the release system can provide a method for controlling the release rate of the molecules. The molecules can be homogeneously or heterogeneously distributed within the release system. Selection of the release system is dependent on the desired rate of release of the molecules.

Both non-degradable and degradable release systems can be used for delivery of molecules. Suitable release systems include polymers, polymeric matrices, non-polymeric matrices, and inorganic and organic excipients and diluents. Examples of such excipients and diluents include calcium carbonate and sugar. Release systems may be natural or synthetic, although synthetic release systems are preferred due to the better characterization of release profiles. The release system is selected based on the period over which release is desired, generally in the range of at least one to twelve months for in vivo applications. In contrast, release times as short as a few seconds may be desirable for some in vitro applications. In some cases, continuous (constant) release from a reservoir may be most useful. In other cases, pulsed (variable) release from a reservoir may provide results that are more effective.

Pulsatile release can be achieved from an individual reservoir, from a plurality of reservoirs, or a combination thereof. For example, where each reservoir provides only a single pulse, multiple pulses (i.e. pulsatile release) are achieved by temporally staggering the single pulse release from each of several reservoirs. Alternatively, multiple pulses can be achieved from a single reservoir by incorporating several layers of a release system and other materials into a single reservoir.

Continuous release can be achieved by incorporating a release system that degrades, dissolves, or allows diffusion of molecules through it over an extended period. In addition, continuous release can be approximated by releasing several pulses of molecules in rapid succession ("digital" release, analogous to the digital storage and reproduction of music).

Active and passive release systems can be combined. For example, a metal film or membrane reservoir cap, which is removed actively, can cover a passive release system that only begins its passive release after the metal film has been actively removed. Alternatively, a given substrate can include both passive and active release reservoirs.

The release system material can be selected so that molecules of various molecular weights are released from a reservoir by diffusion out or through the material or degradation of the material. Biodegradable polymers, bioerodible hydrogels, and protein delivery systems are preferred for release of molecules by diffusion, degradation, or dissolution. In general, these materials degrade or dissolve either by enzymatic hydrolysis or exposure to water in vivo or in vitro, or by surface or bulk erosion. Representative synthetic, biodegradable polymers include polyamides such as poly(amino acids) and polypeptides; polyesters such as poly(lactic acid), poly(glycolic acid), poly(lactic-co-glycolic acid), and polycaprolactone; polyanhydrides; poly-orthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include polyethers such as poly(ethylene oxide), poly(ethylene glycol), and poly(tetramethylene oxide); vinyl polymers—polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); polyurethanes; cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Secondary Devices

As used herein, unless explicitly indicated otherwise, the term "secondary device" includes, but is not limited to, any device and component thereof which can be located in or designed to operably communicate with one or more reservoirs in a microchip device. In a preferred embodiment, the secondary device is a sensor or sensing component. As used herein, a "sensing component" includes, but is not limited to, a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Secondary devices are further described in PCT WO 01/64344.

Examples of sensing components include components utilized in measuring or analyzing the presence, absence, or change in a drug, chemical, or ionic species, energy (or light), or one or more physical properties (e.g., pH, pressure) at a site. In a preferred embodiment, the microchip device is implantable in a patient (e.g., a human or other mammal) and includes sensors for monitoring the levels of glucose or urea in blood and other body fluids.

There are several different options for receiving and analyzing data obtained with devices located in the microchip devices. Typically, the operation of the microchip system will be controlled by an on-board (i.e. within the package) microprocessor. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the microchip system locally by a microbattery or remotely by wireless transmission.

D. Reservoir Caps

The reservoir cap is positioned on the reservoir over the molecules to be released. In one embodiment, a reservoir cap is positioned on top of the release systems contained in one or more reservoirs.

Metal Films

In a preferred embodiment, the reservoir cap is in the form of a thin metal film (also herein referred to as a metal membrane). Representative examples, of suitable metal materials include copper, gold, silver, zinc, and combinations thereof. The reservoir cap optionally can be coated with an overcoat material, for example to protect the metal from premature degradation until the overcoat material has been substantially removed by dissolving, eroding, biodegrading, oxidizing, or otherwise degrading, such as upon exposure to water in vivo or in vitro. Representative suitable degradable materials include synthetic or natural biodegradable polymers.

The metal films may be reinforced with a pattern of a second material (frequently dissimilar to the metal) deposited onto surfaces of the film in order to strengthen the film and/or to distribute mechanical stress. The second material can be deposited on the surface adjacent the reservoir (i.e. the inner surface) or distal the reservoir (i.e. the outer surface).

For thermal disintegration, the reservoir cap can be a non-conducting material.

E. Device Packaging, Control Circuitry, and Power Source

Microelectronic device packages are typically made of an insulating or dielectric material such as aluminum oxide or silicon nitride. Their purpose is to allow all components of the device to be placed in close proximity and to facilitate the interconnection of components to power sources and to each other. For in vivo applications of the delivery device, the entire package, including all components (i.e. the device, the microprocessor, and the power source), are contained, coated, or encapsulated in a biocompatible material such as poly(ethylene glycol), polytetrafluoroethylene-like materials, or titanium. The materials requirements for in vitro applications may be less stringent and depend on the particular situation.

The control circuitry typically consists of a timer, a demultiplexer, a microprocessor, an input source (for example, a memory source, a signal receiver or a biosensor), and a power source. The timer and demultiplexer circuitry can be designed and incorporated directly onto the surface of the microchip during electrode fabrication. The criteria for selection of a microprocessor are small size, low power requirement, and the ability to translate the output from memory sources, signal receivers, or biosensors into an address for the direction of power through the demultiplexer to a specific reservoir on the delivery device. Selection of a source of input to the microprocessor such as memory sources, signal receivers, or biosensors depends on the delivery device's particular application and whether device operation is preprogrammed, controlled by remote means, or controlled by feedback from its environment (i.e. biofeedback).

The criteria for selection of a power source are small size, sufficient power capacity, ability to be integrated into the control circuitry, ability to be recharged, and the length of time before recharging is necessary. Several lithium-based, rechargeable microbatteries have been described in Jones & Akridge, "Development and performance of a rechargeable thin-film solid-state microbattery", *J. Power Sources,* 54:63–67 (1995); and Bates et al., "New amorphous thin-film lithium electrolyte and rechargeable microbattery", *IEEE 35th International Power Sources Symposium,* pp. 337–39 (1992). These batteries are typically only ten microns thick and occupy 1 $cm^2$ of area. One or more of these batteries can be incorporated directly onto the delivery device. Alternatively, a capacitor can be charged by transduction of microwave, RF, or sonic energy.

V. Methods of Device Fabrication

The microchip devices can be made using the methods described below, alone or in combination with known methods, such the microfabrication techniques described in U.S. Pat. Nos. 5,797,898 and 6,123,861, to Santini, et al. Other methods are described in PCT WO 01/41736. For example, the substrate can be formed from polymer, ceramic, or metal, e.g., by compression molding powders or slurries of polymer, ceramic, metal, or combinations thereof. Other forming methods useful with these materials include injection molding, thermoforming, casting, machining, and other methods known to those skilled in the art. Substrates formed using these methods can be formed (e.g., molded) to have the reservoirs or the reservoirs can be added in subsequent steps, such as by etching.

Exemplary processes are described below.

A. Fabrication of Substrates with Reservoirs

In one method of microchip manufacture, fabrication begins by depositing and photolithographically patterning a material, typically an insulating or dielectric material, onto the substrate to serve as an etch mask during reservoir etching. Typical insulating materials for use as a mask include silicon nitride, silicon dioxide, and some polymers, such as polyimide. In a preferred embodiment, a thin film (approximately 1000–3000 Å) of low stress, silicon-rich nitride is deposited on both sides of a silicon wafer in a Vertical Tube Reactor (VTR). Alternatively, a stoichiometric, polycrystalline silicon nitride ($Si_3N_4$) can be deposited by Low Pressure Chemical Vapor Deposition (LPCVD), or amorphous silicon nitride can be deposited by Plasma Enhanced Chemical Vapor Deposition (PECVD). Reservoirs are patterned into the silicon nitride film on one side of the wafer by ultraviolet photolithography and either plasma etching or a chemical etch consisting of hot phosphoric acid or buffered hydrofluoric acid. The patterned silicon nitride serves as an etch mask for the chemical etching of the exposed silicon by a concentrated potassium hydroxide solution (approximately 20–40% KOH by weight at a temperature of 75–90° C.). Alternatively, the reservoirs can be etched into the substrate by dry etching techniques such as reactive ion etching or ion beam etching. These techniques are commonly used in the fabrication of microelectronic devices, as reviewed, for example, by Wolf et al. (1986), Jaeger (1988), and Madou (1997). Use of these microfabrication techniques allows the incorporation of hundreds to thousands of reservoirs on a single microchip. The spacing between each reservoir depends on its particular application and whether the device is a passive or active device. In a passive device, the reservoirs may be less than one micron apart. In an active device, the distance between the reservoirs may be slightly larger (greater than approximately 1 to 10 $\mu$m) due, for example to the space occupied by circuitry on or near each reservoir. Reservoirs can be made in nearly any shape and depth, and need not pass completely through the substrate. In a preferred embodiment, the reservoirs are etched into a (100) oriented, silicon substrate by potassium hydroxide, in the shape of a square pyramid having side walls sloped at 54.7°, and pass completely through the substrate (approximately 525 $\mu$m thick) to the silicon nitride film on the other side of the substrate, forming a silicon nitride membrane. (Here, the silicon nitride film serves as a potassium hydroxide etch stop.) The pyramidal shape allows easy filling of the reservoirs through the large opening of the reservoir (approximately 800 $\mu$m by 800 $\mu$m for a 525 $\mu$m thick wafer) on the patterned side of the substrate, release through the small opening of the reservoir (approximately 50 $\mu$m by 50 $\mu$m) on the other side of the substrate, and provides a large cavity inside the device for storing the drugs or other molecules to be delivered.

In a preferred embodiment of the active devices, resistors are integrated into the device. Typically, thin-film resistors are conveniently integrated with the reservoir during the manufacturing process, as the resistors commonly are made by deposition and patterning methods that are used to manufacture the reservoirs as described herein. Alternatively, small chip resistors can be surface mounted in close proximity to the reservoir.

B. Fabrication of Active Timed-Release Reservoir Caps

In a preferred embodiment, photoresist is patterned in the form of electrodes on the surface of the substrate having the reservoirs covered by the thin membrane of insulating or dielectric material. The photoresist is developed such that the area directly over the covered opening of the reservoir is left uncovered by photoresist and is in the shape of an anode. A thin film of conductive material capable of dissolving into solution or forming soluble ions or oxidation compounds upon the application of an electric potential is deposited over the entire surface using deposition techniques such as chemical vapor deposition, electron or ion beam evaporation, sputtering, spin coating, and other techniques known in the art. Exemplary materials include metals such as copper, gold, silver, and zinc, and some polymers, such as disclosed by Kwon et al. (1991) and Bae et al. (1994). After film deposition, the photoresist is stripped from the substrate. This removes the deposited film, except in those areas not covered by photoresist (lift-off technique). This leaves conducting material on the surface of the substrate in the form of electrodes. An alternative method involves depositing the conductive material over the entire surface of the device, patterning photoresist on top of the conductive film using UV or infrared (IR) photolithography, so that the photoresist lies over the reservoirs in the shape of anodes, and etching the unmasked conductive material using plasma, ion beam, or chemical etching techniques. The photoresist is then stripped, leaving conductive film anodes covering the reservoirs. The thickness of the conductive film typically, but not necessarily, is between about 0.05 and several microns. The anode serves as the reservoir cap and the placement of the cathodes on the device is dependent upon the device's application and method of electric potential control.

Alternatively, a reservoir cap material can be deposited that disintegrates, cracks, or ruptures in response to changes in the temperature of the cap material itself or in response to a temperature-induced pressure increase in the reservoir. Such caps can be made using techniques such as, but not limited to, spin coating, solvent casting, evaporation, chemical vapor deposition, sputtering, or other deposition methods known in the art. The contents of such as reservoir contains at least one material that expands or vaporizes when exposed to heat produced by a source within or in thermal communication with the reservoir or the material. Representative examples of such sources that can transmit energy to the material include resistive heating elements, piezoelectric elements, capacitive discharge (spark) elements, and combinations thereof.

An insulating or dielectric material such as silicon oxide ($SiO_x$) or silicon nitride ($SiN_x$) is deposited over the entire surface of the device by methods such as chemical vapor deposition (CVD), electron or ion beam evaporation, sputtering, or spin coating. Photoresist is patterned on top of the dielectric to protect it from etching except on the cathodes and the portions of the anodes directly over each reservoir. The dielectric material can be etched by plasma, ion beam, or chemical etching techniques. The purpose of this film is to protect the electrodes from corrosion, degradation, or dissolution in all areas where electrode film removal is not necessary for release.

The electrodes are positioned in such a way that when an electric potential is applied between an anode and a cathode, the unprotected (not covered by dielectric) portion of the anode reservoir cap oxidizes to form soluble compounds or ions that dissolve into solution, exposing the reservoir contents to the surrounding fluids. The molecules are released from the reservoir at a rate dependent upon the degradation or dissolution rate of a degradable release system or the rate of diffusion of the molecules out of or through a non-degradable release system.

Alternatively, one or more resistors are positioned in the reservoirs or near the cap material so that passing a current through the resistor will change the temperature of the contents of the reservoir or the temperature of the cap material. A sufficient temperature change causes the reservoir to open by rupturing the cap due to an increase in the pressure in the reservoir, a change in the cap material itself based on its physical properties (e.g. volume changes with temperature related to its coefficient of thermal expansion), or a combination thereof.

C. Removal of the Insulator Membrane (Reservoir Etch Stop)

The thin membrane of insulating or dielectric material covering the reservoir used as a mask and an etch stop during reservoir fabrication must be removed from the active timed release device before filling the reservoir and from the passive timed release device (if the reservoir extends completely through the substrate) after filling reservoir. The membrane may be removed in two ways. First, the membrane can be removed by an ion beam or reactive ion plasma. In a preferred embodiment, the silicon nitride used as the insulating material can be removed by reactive ion plasma composed of oxygen and fluorine containing gases such as $CHF_3$ or $CF_4$. Second, the membrane can be removed by chemical etching. For example, buffered hydrofluoric acid (BHF or BOE) can be used to etch silicon dioxide and hot phosphoric acid can be used to etch silicon nitride.

D. Reservoir Filling

The release system containing the molecules for delivery is inserted into the large opening of the reservoir by injection, inkjet printing, screen printing, or spin coating. Each reservoir can contain a different molecule and dosage. Similarly, the release kinetics of the molecule in each reservoir can be varied by the choice of the release system and cap materials. In addition, the mixing or layering of release system and cap materials in each reservoir can be used to tailor the release kinetics to the needs of a particular application.

The distribution over the microchip of reservoirs filled with the release system containing the molecules to be delivered can vary depending on the medical needs of the patient or other requirements of the system. For applications in drug delivery, for example, the drugs in each of the rows can differ from each other. One row may contain a hormone and another row may contain a metabolite. In addition, the release system can differ within each row to release a drug at a high rate from one reservoir and a slow rate from another reservoir. The dosages can also vary within each row. For those devices having deep (greater than 10 $\mu$m) reservoirs or reservoirs with large (greater than 50 $\mu$m) openings, differences in reservoir loading can be achieved by injection or inkjet printing of different amounts of material directly into each reservoir. Variation between reservoirs is achieved in devices having shallow (less than 10 $\mu$m) reservoirs, reservoirs that do not pass completely through the substrate, or reservoirs with small (less than 50 $\mu$m) openings by a repeated, step-wise process of masking selected reservoirs, spin coating, and etching, as described above regarding the fabrication by spin coating of passive timed release reservoir caps. Preferably, the release system and molecules to be delivered are mixed before application to the reservoirs. Although injection, inkjet printing and spin coating are the preferred methods of filling reservoirs, it is understood that each reservoir can be filled individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

E. Device Packaging, Control Circuitry, and Power Source

The openings through which the reservoirs of passive and active devices are filled are sealed by wafer bonding or with a waterproof epoxy or other appropriate material impervious to the surrounding fluids. For in vitro applications, the entire unit, except for the face of the device containing the reservoirs and electrodes, is encased in a material appropriate for the system. For in vivo applications, the unit is preferably encapsulated in a biocompatible material such as poly (ethylene glycol) or polytetrafluoroethylene.

The mechanism for release of molecules by the active timed-release device does not depend on multiple parts fitted or glued together which must retract or dislodge. Control of the time of release of each reservoir can be achieved by a preprogrammed microprocessor, by remote control, by a signal from a biosensor, or by any combination of these methods.

First, a microprocessor is used in conjunction with a source of memory such as programmable read only memory (PROM), a timer, a demultiplexer, and a power source such as a microbattery, which is described, for example, by Jones et al. (1995) and Bates et al. (1992). The pre-selected release pattern is written in machine-readable form directly into the PROM by the user (e.g., the physician). These instructions are read from the PROM by the microprocessor, which takes appropriate action, such as starting a timer. When the time for release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor. A microbattery provides the power to operate the PROM, timer, and microprocessor, and provides the electric potential or current input that is directed to a particular reservoir by the demultiplexer. The manufacture, size, and location of each of these components are dependent upon the requirements of a particular application. In a preferred embodiment, the memory, timer, microprocessor, and demultiplexer circuitry is integrated directly onto the surface of the chip. The microbattery is attached to the other side of the chip and is connected to the device circuitry by vias or thin wires. However, in some cases, it is possible to use separate, prefabricated, component chips for memory, timing, processing, and demultiplexing. These are attached to the backside of the miniaturized delivery device, or carrier substrate, with the battery. The size and type of prefabricated chips used depends on the overall dimensions of the delivery device and the number of reservoirs.

Second, activation of a particular reservoir by the application of an electric potential or current can be controlled externally by remote control. Much of the circuitry used for remote control is the same as that used in the preprogrammed method. The main difference is that the function of the PROM as a source of the dosing regime is replaced by a signal receiver. A signal (e.g., radio wave, microwave, low power laser, or ultrasound) is sent to the receiver by an external source, for example, a computer or an ultrasound generator. The signal is received by the microprocessor where it is translated into a reservoir address. Power is then directed through the demultiplexer to the reservoir having the appropriate address.

Third, a biosensor, which may or may not be integrated into the microchip, can detect molecules in the surrounding fluids or temperature or pressure. When the concentration of the molecules reaches a certain value or when a tissue temperature or fluid pressure is reached, the sensor sends a signal to the microprocessor to activate one or more reservoirs. The microprocessor directs power through the demultiplexer to the particular reservoir(s).

F. Electric Potential or Current Control Methods

The reservoir caps of an active device are anodes that oxidize to form soluble compounds and ions when a potential is applied between the anode and a cathode. For a given electrode material and electrolyte, there exists a range of electric potentials over which these oxidation reactions are thermodynamically and kinetically favorable. In order to reproducibly oxidize and open the reservoir caps of the device, the anode potential must be maintained within this favorable potential range.

There exist two primary control methods for maintaining an electrode within a specific potential range. The first method is called potentiostatic control. As the name indicates, the potential is kept constant during reservoir activation. Control of the potential is typically accomplished by incorporating a third electrode into the system that has a known, constant potential, called a reference electrode. The reference electrode can take the form of an external probe whose tip is typically placed within one to three millimeters of the anode surface. The potential of the anode is measured and controlled with respect to the known potential of a reference electrode such as a saturated calomel electrode (SCE), a silver/silver chloride (Ag/AgCl) electrode, or sometimes a platinum wire. In a preferred embodiment of potentiostatic control, a thin film reference electrode and potential feedback controller circuitry could be fabricated directly onto the surface of the microchip. For example, a microfabricated Ag/AgCl reference electrode integrated with a microchip device would enable the device to maintain the anode potential of an activated reservoir within the oxidation regime until the reservoir was completely opened. The second method is called galvanostatic control. As the name indicates, the current is kept constant during reservoir activation. One drawback of this method of control is that there is more than one stable potential for a given current density. However, if the current density versus potential behavior is well characterized for the microchip device in a particular electrolyte system, the current density that will maintain the anode in the oxidation regime will be known. In this case, the galvanostatic method of potential control would be preferable to the potentiostatic control, because galvanostatic control does not require a reference electrode.

Alternatively, corrosion can be achieved using less complicated means of controlling the potential. A reference electrode is not needed if the potential between the anode and the cathode is periodically swept through a range of potential such that the potential difference between the anode and the electrolyte needed for oxidative corrosion is achieved during the sweep. In other words, if the reference electrode is eliminated and the electrical potential is swept back and forth (i.e. cycled) over a suitable range, then the anode will experience the potential required for corrosion at least a fraction of the time. Corrosion will thus occur.

Another method of reservoir opening and chemical release is based on rupturing the reservoir cap due to a change in the temperature of the materials in the reservoir or a change in the temperature of the material forming the reservoir cap. In a preferred embodiment, such temperature changes are induced using thin film resistors integrated onto the microchip itself or small, prefabricated chip resistors surface mounted onto the microchip or its associated packaging. The temperature change may be controlled by the amount of current that is passed through the resistor and the thermal properties of the material inside the reservoir or the reservoir cap material. Control over the amount of current applied and its duration of application can be controlled by a microprocessor, remote control, biosensor, or a combination of these devices.

VI. Microchip Device Applications

The microchip device systems can be used in a wide variety of applications. The applications can be ex vivo or in vitro, but more preferably are for in vivo applications, particularly following non- or minimally-invasive implantation.

Preferred applications for using the devices and systems include the controlled delivery of a drug to sites within the body of a human or animal, biosensing, or a combination thereof. The microchip systems are especially useful for drug therapies in which it is desired to control the exact amount, rate, and/or time of delivery of the drug. Preferred drug delivery applications include the delivery of potent compounds, including both small and large molecules, such as hormones, steroids, chemotherapy medications, vaccines, gene delivery vectors, and some strong analgesic agents.

The microchips can be implanted into the body of a human or other animal via surgical procedures or injection, or swallowed, and can deliver many different drugs, at varying rates and varying times. In another embodiment, the microchip device includes one or more biosensors (which may be sealed in reservoirs until needed for use) that are capable of detecting and/or measuring signals within the body of a patient. As used herein, the term "biosensor" includes, but is not limited to, sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as blood gases, drug concentration, or temperature.

The system also has a variety uses that are not limited to implantation. For example, the reservoir contents may include a sensor for detecting a chemical or biological molecule at the site in which the microchip is placed, and the telemetry system transmits a status of the sensor detection to the remote controller. Such a site could be in vivo or in vitro. The chemical or biological molecule could, for example, be associated with a chemical or biological weapon, and the system used in an early warning/detection system.

Active microchip devices may be controlled by local microprocessors or remote control. Biosensor information may provide input to the controller to determine the time and type of activation automatically, with human intervention, or a combination thereof. The microchip devices have numerous in vivo, in vitro, and commercial diagnostic applications. The microchips are capable of delivering precisely metered quantities of molecules and thus are useful for in vitro applications, such as analytical chemistry and medical diagnostics, as well as biological applications such as the delivery of factors to cell cultures.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A microchip device for the controlled release or exposure of molecules or secondary devices comprising:
   a substrate;
   a plurality of reservoirs in the substrate;
   reservoir contents comprising molecules, a secondary device, or both, located in the reservoirs;
   reservoir caps positioned on the reservoirs over the reservoir contents;
   electrical activation means for disintegrating the reservoir cap to initiate exposure or release of the reservoir contents in selected reservoirs; and
   a current distribution means, operably engaged with or integrated into each reservoir cap, to enhance reservoir cap disintegration,
   wherein the current distribution means comprises a structure selected from the group consisting of structures for dispersing electrical current uniformly across each reservoir cap, structures for dispersing thermal energy uniformly across each reservoir cap, structures for increasing the exchange current density of each reservoir cap which operates as an electrode, and combinations thereof.

2. The device of claim 1, further comprising an cathode, wherein the reservoir caps each comprise a thin metal film which is an anode, the electrical activation means comprises a means for applying an electric potential between the cathode and the anode effective to cause the reservoir cap disintegration to occur electrochemically.

3. The device of claim 1, wherein the current distribution means comprises a current distribution network mounted on or integrated into the reservoir cap.

4. The device of claim 3, wherein the current distribution network comprises a plurality of traces fabricated onto a surface of the reservoir cap.

5. The device of claim 4, wherein the traces comprise a non-metal, conducting material.

6. The device of claim 4, wherein the traces comprise a metal.

7. The device of claim 6, wherein the reservoir cap comprises a thin metal film, the metal of which is the same as or different from the metal of the traces.

8. The device of claim 4, wherein the traces are coated with a passivating layer.

9. The device of claim 1, wherein the current distribution means comprises an electrochemically plated metal layer on the outer surface of the reservoir cap, said metal layer having increased surface roughness relative to said outer surface of the reservoir cap.

10. The device of claim 2, wherein the outer surface of the reservoir cap has been treated to increase the surface roughness of the outer surface.

11. The device of claim 1, wherein the reservoir contents comprise a drug.

12. The device of claim 1, wherein the reservoir contents comprises a secondary device.

13. The device of claim 1, wherein the electrical activation means comprises a microprocessor.

14. The device of claim 13, wherein the electrical activation means further comprises a power source.

15. A method of delivering reservoir contents to a site comprising:
   providing the microchip device of claim 1 at a delivery site; and
   activating said electrical activation means to initiate release of the reservoir contents from selected reservoirs of the microchip device.

16. A device for the controlled release or exposure of molecules or secondary devices comprising:
   a substrate;
   a plurality of reservoirs in the substrate;
   reservoir contents comprising molecules, a secondary device, or both, located in the reservoirs;
   reservoir caps positioned on the reservoirs over the reservoir contents;
   electrical activation means for disintegrating the reservoir cap to initiate exposure or release of the reservoir contents in selected reservoirs;
   at least one resistor operably adjacent the reservoir caps, wherein the electrical activation means comprises a means for applying an electric current through the resistor effective to cause the reservoir cap disintegration to occur thermally; and
   a current distribution means or both a current distribution means and a stress induction means, operably engaged with or integrated into each reservoir cap, to enhance reservoir cap disintegration.

17. A device for the controlled release or exposure of molecules or secondary devices comprising:
   a substrate;
   a plurality of reservoirs in the substrate;
   reservoir contents comprising molecules, a secondary device, or both, located in the reservoirs;
   reservoir caps positioned on the reservoirs over the reservoir contents;
   electrical activation means for disintegrating the reservoir cap to initiate exposure or release of the reservoir contents in selected reservoirs; and
   a stress induction means operably engaged with or integrated into the reservoir cap, to enhance reservoir cap disintegration,
   wherein the stress induction means comprises a pre-stressed structure attached to or integrated into the reservoir cap, the pre-stressed structure providing a force substantially perpendicular to the surface of the reservoir cap.

18. The device of claim 17, wherein the pre-stressed structure comprises a bilayer cantilever beam.

19. The device of claim 17, wherein the pre-stressed structure comprises a single layer of material, the layer having a stress gradient.

20. The device of claim 17, wherein the pre-stressed structure comprises a spring, coil, or cross design.

21. The device of claim 17, wherein the reservoir contents comprise drug molecules for release.

22. A device for the controlled release of molecules comprising:

a substrate;

a plurality of reservoirs in the substrate, each reservoir containing drug molecules for release;

a plurality of reservoir caps which comprise a thin metal film, enclosing each reservoir;

an electrical power source for selectively disintegrating each reservoir cap to release of the drug molecules; and a current distribution network comprising a plurality of traces attached to a surface of the thin metal film of each reservoir cap.

23. The device of claim 22, wherein the traces comprise a corrodible material.

24. The device of claim 22, wherein the traces comprise a non-corrodible material.

25. The device of claim 22, wherein the traces are formed substantially of the same material as the material from which the reservoir caps are formed.

26. The device of claim 22, wherein the traces are formed substantially of a different material as the material from which the reservoir caps are formed.

27. A method for enhancing disintegration of a reservoir cap of a microchip device, the method comprising:

activating an electrical means to initiate disintegration of at least one reservoir cap located in a microchip device which comprises a substrate having a plurality of reservoirs, each reservoir having a reservoir cap positioned thereon, each reservoir containing molecules or secondary devices for controlled release or exposure; and operating a current distribution means or a stress induction means or both a current distribution means and a stress induction means, operably engaged with or integrated into each reservoir cap, to enhance corrosion, internal stress, or both, of the reservoir cap.

* * * * *

UNITED STATES PATENT AND TRADEMARK OFFICE
CERTIFICATE OF CORRECTION

PATENT NO. : 6,875,208 B2  Page 1 of 1
DATED : April 5, 2005
INVENTOR(S) : Santini, Jr. et al.

It is certified that error appears in the above-identified patent and that said Letters Patent is hereby corrected as shown below:

<u>Column 1,</u>
Line 9, please insert the following heading and paragraph:

-- STATEMENT REGARDING FEDERALLY SPONSORED RESEARCH OR DEVELOPMENT

This invention was made with government support under Grant Number AI047739, awarded by NIH. The government has certain rights in the invention. --.

Signed and Sealed this

Twenty-ninth Day of November, 2005

JON W. DUDAS
*Director of the United States Patent and Trademark Office*